United States Patent
Ackley et al.

(10) Patent No.: US 9,734,360 B2
(45) Date of Patent: Aug. 15, 2017

(54) APPARATUS AND METHOD FOR APPLYING BAR CODES TO PELLET-SHAPED ARTICLES

(71) Applicant: Ackley Machine Corporation, Moorestown, NJ (US)

(72) Inventors: E. Michael Ackley, Mannington, NJ (US); Daniel J. Palmer, North Wales, PA (US)

(73) Assignee: Ackley Machine Corporation, Moorestown, NJ (US)

( * ) Notice: Subject to any disclaimer, the term of this patent is extended or adjusted under 35 U.S.C. 154(b) by 0 days.

(21) Appl. No.: 15/181,063

(22) Filed: Jun. 13, 2016

(65) Prior Publication Data

US 2016/0292465 A1 Oct. 6, 2016

Related U.S. Application Data

(60) Continuation of application No. 13/374,184, filed on Dec. 15, 2011, now abandoned, which is a division of application No. 11/629,512, filed as application No. PCT/US2005/020860 on Jun. 13, 2005, now Pat. No. 8,102,520.

(60) Provisional application No. 60/578,823, filed on Jun. 14, 2004.

(51) Int. Cl.
| | |
|---|---|
| *B41F 17/36* | (2006.01) |
| *G06K 1/12* | (2006.01) |
| *B07C 5/34* | (2006.01) |
| *B41J 2/01* | (2006.01) |
| *G06K 19/06* | (2006.01) |

(52) U.S. Cl.
CPC ............ *G06K 1/121* (2013.01); *B07C 5/3412* (2013.01); *B41F 17/36* (2013.01); *B41J 2/01* (2013.01); *G06K 19/06028* (2013.01); *G06K 19/06037* (2013.01)

(58) Field of Classification Search
CPC ............. B41F 17/36; G06K 19/06028; G06K 19/06037; G06K 19/06121; G06K 19/06056; G06K 19/06168; G06K 19/06159; G06K 19/06178; A61J 2205/10; A61J 2205/50
USPC ........................................................ 101/38.1
See application file for complete search history.

(56) References Cited

U.S. PATENT DOCUMENTS

| | | | |
|---|---|---|---|
| 3,618,764 A | 11/1971 | Bawduniak | |
| 3,751,277 A | 8/1973 | Small et al. | |
| 3,802,340 A * | 4/1974 | Braun | ..................... B41F 17/36 101/154 |
| 4,143,770 A | 3/1979 | Grimmell et al. | |
| 4,548,825 A | 10/1985 | Voss et al. | |
| 4,893,253 A | 1/1990 | Lodder | |
| 5,085,510 A | 2/1992 | Mitchell | |

(Continued)

OTHER PUBLICATIONS

International Search Report for PCT/US2005/020860 mailed Feb. 10, 2006.

*Primary Examiner* — Leslie J Evanisko
(74) *Attorney, Agent, or Firm* — Nixon & Vanderhye, P.C.

(57) ABSTRACT

A conveyer mechanism (110) may include one or more composition inspection units provided along the intended product transport path. The product's composition, e.g., it's ink composition, is compared with a predetermined standard, to determine whether the product is acceptable. A bar code (48, 45.1, 47.1, 85) may be provided to an external surface of the article for identification/traceability purposes.

10 Claims, 8 Drawing Sheets

(56) References Cited

U.S. PATENT DOCUMENTS

| | | |
|---|---|---|
| 5,376,771 A | 12/1994 | Roy |
| 5,481,100 A * | 1/1996 | Terauchi .......... G06K 19/06028 235/470 |
| 5,679,954 A | 10/1997 | Soloman |
| 5,683,786 A | 11/1997 | Kavanaugh |
| 5,700,998 A | 12/1997 | Palti |
| 5,746,323 A | 5/1998 | Dragotta |
| 5,845,264 A | 12/1998 | Nellhaus |
| 5,894,801 A | 4/1999 | Ackley |
| 5,900,634 A | 5/1999 | Soloman |
| 5,992,742 A | 11/1999 | Sullivan et al. |
| 6,314,876 B1 | 11/2001 | Ackley |
| 6,348,090 B1 | 2/2002 | Grillo et al. |
| 6,481,347 B2 * | 11/2002 | Ackley .................. B41F 17/36 101/35 |
| 6,543,692 B1 | 4/2003 | Nellhause et al. |
| 6,677,296 B2 * | 1/2004 | Bonsall .............. C11D 17/0073 101/35 |
| 6,776,341 B1 | 8/2004 | Sullivan et al. |
| 6,799,725 B1 | 10/2004 | Hess et al. |
| 6,862,128 B2 | 3/2005 | Katase |
| 7,102,741 B2 | 9/2006 | Ackley, Jr. et al. |
| 7,166,154 B2 | 1/2007 | Barreto |
| 7,370,797 B1 | 5/2008 | Sullivan et al. |
| 7,827,911 B2 | 11/2010 | Kettinger et al. |
| 7,891,565 B2 | 2/2011 | Pinchen et al. |
| 8,080,097 B2 | 12/2011 | Chinea et al. |
| 2002/0118366 A1 | 8/2002 | Baldwin |
| 2003/0180357 A1 | 9/2003 | Martino et al. |
| 2004/0219109 A1 | 11/2004 | Hatch |
| 2005/0099475 A1 | 5/2005 | Barreto |
| 2006/0226234 A1 | 10/2006 | Kettinger et al. |
| 2006/0278104 A1 * | 12/2006 | Boyce .................... B41F 17/36 101/35 |
| 2007/0012783 A1 | 1/2007 | Mercolino |
| 2007/0062385 A1 | 3/2007 | Kettinger et al. |
| 2007/0134327 A1 | 6/2007 | Flanner et al. |
| 2008/0290168 A1 | 11/2008 | Sullivan et al. |
| 2009/0059214 A1 | 3/2009 | Ackley, Jr. et al. |
| 2009/0075261 A1 | 3/2009 | Hayward et al. |
| 2010/0330169 A1 | 12/2010 | Bunick et al. |
| 2011/0068511 A1 | 3/2011 | Sowden et al. |
| 2012/0132722 A1 | 5/2012 | Ackley, Jr. et al. |

* cited by examiner

APPARATUS AND METHOD FOR APPLYING BAR CODES TO PELLET-SHAPED ARTICLES

CROSS-REFERENCE TO APPLICATION

This application is a continuation of U.S. application Ser. No. 13/374,184, filed Dec. 15, 2011, now abandoned, which is a divisional of U.S. application Ser. No. 11/629,512, filed Dec. 14, 2006, now U.S. Pat. No. 8,102,520, which is a 371 of international application PCT/US2005/020860 filed 13 Jun. 2005, which designated the U.S. and claims the benefit of U.S. provisional application Ser. No. 60/578,823 filed 14 Jun. 2004, each incorporated by reference in its entirety. U.S. non-provisional patent application Ser. No. 10/705,821, filed Nov. 13, 2003, now U.S. Pat. No. 7,102,741, is incorporated herein by reference in its entirety.

BACKGROUND OF THE INVENTION

1. Field of the Invention

The present invention relates to processing of pellet-shaped articles, for example, pharmaceuticals such as caplets and tablets. In particular, the present invention relates to methods and systems for inspecting and/or identifying pharmaceutical articles.

2. Description of Related Art

Inspection of pellet-shaped articles is known in the art. Inspection units are typically configured to inspect and remove pellet-shaped articles from a conveyer mechanism that have been improperly processed in a previous processing operation. Previous processing operations may include marking the pellet-shaped articles with printing indicia, coloring the pellet-shaped articles, laser drilling holes in the pellet-shaped articles, and/or gel-coating the pellet-shaped articles. These processing operations are typically completed upstream from the inspection unit such that the inspection unit may inspect if these processes have been properly completed.

One concern among manufacturers is to ensure that the composition of the pellet-shaped articles remains consistent. For example, the introduction of foreign substances into one or more of the pellet-shaped articles that may cause harm to the patient.

In another example, a variety of known devices have been developed for applying a gel coating to pellet-shaped articles. Typically, the pellet-shaped articles, e.g., tablets, capsules, caplets and pills, are coated by having one side of the pellet-shaped article coated at a time. Often, due to a processing error, one or both sides of the pellet-shaped article are not coated at all, or one side of the pellet-shaped article is coated twice. As a result, the pellet-shaped article has at least one side that is not properly coated with gel. It is important for the manufacturer to carefully inspect the pellet-shaped articles for defects, such as an improperly coated side of the article, before the pellet-shaped article is distributed to the consumer so as to ensure the quality of the product and hence protect the safety of the consumer. An example of an inspection unit is shown in U.S. Pat. No. 5,085,510.

U.S. Pat. No. 5,894,801 to Ackley, Jr., incorporated herein by reference in its entirety, describes a method and apparatus for conveying a plurality of pellet-shaped articles, such as pharmaceuticals. The conveyer conveys the pharmaceuticals past one or more article modifying devices, such as a laser that forms in the pharmaceuticals drilled or blind bore holes that act as a mechanical time-release mechanism. Lasers are known from U.S. Pat. No. 5,376,771, incorporated herein by reference in its entirety.

Furthermore, the tracking and/or identification of pharmaceutical articles is typically carried out by use of bar coding, etc., which is provided on packaging for the article. For example, blister packaging often includes a bar code that is provided to the outer foil layer of the blister packaging. While bar coding is useful, it is open to error, e.g., the wrong article could potentially inserted into to wrong blister package, in which case the blister package would not carry the correct information. Moreover, once the article is removed from the blister package, the bar coding on the package may become meaningless especially in an environment, e.g., hospitals, pharmacies, etc., where multiple articles with different medicines are being handled or dispensed.

Accordingly, a need has developed in the art to provide one or more inspection/identification systems to address the concerns described above.

BRIEF SUMMARY OF THE INVENTION

One aspect of the invention relates to an improved inspection unit for inspecting pellet-shaped articles from a conveyer mechanism. The inspecting unit may take the form of a sensor to analyze the total composition and/or various isolated compositions of each article.

Another aspect of the invention relates to a pellet-shaped article provided with an identifier. The identifier may be provided directly to a surface of the article, and may take the form of a machine-readable code, e.g., a bar code.

Other aspects, features, and advantages of this invention will be described in or become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF PREFERRED EMBODIMENTS

Conveyer Mechanism

Figure 1:
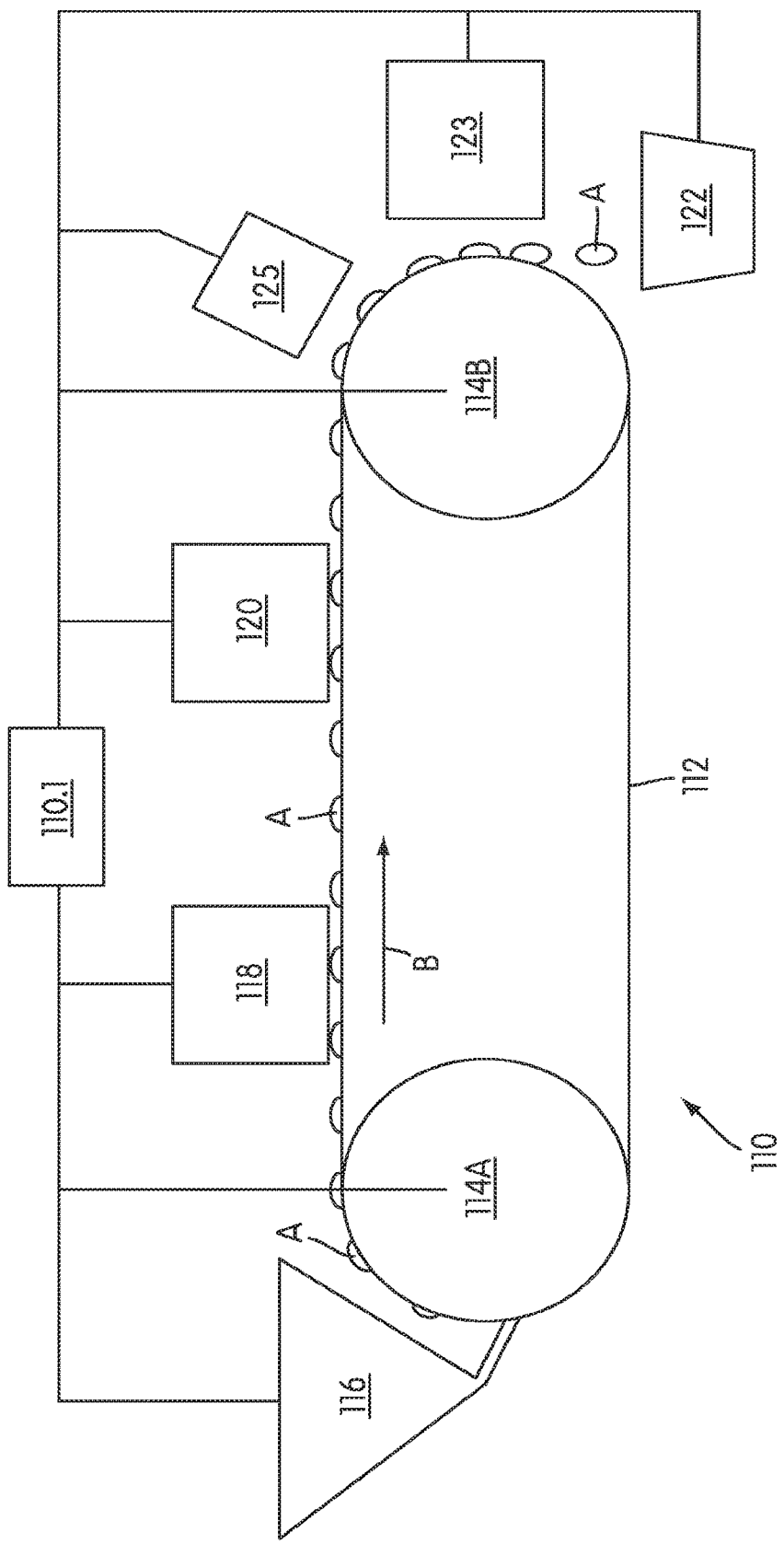
FIG. 1 is a schematic view of an apparatus to convey pellet-shaped articles according to an embodiment of the present invention.

FIG. 1 is a schematic view of a transporting and processing apparatus 110 according to an illustrative embodiment of the present invention. In one example, the transporting and processing apparatus includes a conveyer loop 112 which is entrained about a pair of sprockets 114A and 114B to travel along a transport path in a direction indicated by an arrow B. Other configurations are also contemplated. A dispenser 116, e.g., a hopper, is disposed over the conveyer loop 112 and dispenses articles onto the conveyer loop 112. The articles can be edible or non-edible including confectioneries, non-confectioneries, candies, food, pharmaceuticals or any other discreet type articles. Several dispensers are well known in the art and may be used in embodiments of the present invention, including but not limited to hoppers, rollers and feed dispensers.

The dispenser 116 is positioned adjacent the sprocket 114A which causes the conveyer loop 112 to follow along a predetermined radius of curvature. The conveyer loop 112 travels around a curvilinear path made up of substantially linear sections and substantially non-linear sections, e.g., where the sprockets 114A and 114B are located.

After the dispenser 116 dispenses the articles to the conveyer loop 112, the articles are transported past one or more processing stations 118 and 120. The processing stations may be drilling stations, printing stations or any other process which can be applied to modify the appearance and/or shape of the articles. The processing stations 118 or 120 perform first and second processes on the articles which are coordinated with another, e.g., using a controller 110.1. For example, the first processing station 118 may be a first printer and the second processing station 120 may be a second printer that serially print component images of a composite image on the articles in registered relationship with one another. The processing stations 118 and 120 are preferably located on a portion of the conveyer loop 112 which is substantially linear or not less than a predetermined radius of curvature.

The conveyer loop 112 transports the article towards the sprocket 114B where the articles are inspected by an inspection unit 125. Following inspection, acceptable and non-acceptable articles are separated from one another. For example, rejected articles may be released into a drop-off bin 122, while acceptable articles may be directed to an accept bin 123 or suitable post processing receptacles, such as a blistered package, etc. Of course, the acceptable articles may be routed to the bin 122, while the non-acceptable articles could be routed to bin 123 (i.e., "forcibly" instead of "passively" rejected). The conveyer loop 112 follows this cycle to pick up additional articles from the dispenser 116. The articles may be maintained in a predetermined position, e.g., using the system described in U.S. Pat. No. 6,314,876 to Ackley, Jr., incorporated herein by reference in its entirety.

The above embodiment is only for the purposes of illustration, as other configurations for the transport loop and inspection unit are within the scope of the invention. For example, see the ramp-type conveyer and the inspection units as described in U.S. non-provisional patent application Ser. No. 10/705,821.

The inspection unit 125 can take the form of a near infrared (NIR) spectrometry apparatus, as described in U.S. Pat. Nos. 5,679,954 and 5,900,634, each incorporated herein by reference in its entirety. However, other types of inspection units are possible as well. The inspection unit 125 is structured to determine the composition of an exposed side of the articles A. In one embodiment, in which the processing stations 118, 120 are printers, the inspection unit 125 is configured to determine whether the composition of printing indicia on each of the articles falls within given parameters, i.e., the sensed composition is compared against a predetermined standard. For example, the predetermined standard for a given printed article may be 1-4% printed indicia, while the remaining 96-99% of the article consists of medicine, coatings, etc. The controller may generate a signal indicating that an article is acceptable if the sensed printed indicia is greater than 90-95% of the predetermined standard. In addition, the inspection unit may analyze the printed indicia to determine its composition, and compare the sensed composition against a predetermined standard for the composition. Such an analysis would not necessarily entail an analysis of the amount of printed indicia as a percentage of the total volume or weight of the article.

Furthermore, the inspection unit 125 may include logic or software which can provide an indication of whether the size, shape and consistency of the printed indicia is proper. Moreover, the printed indicia may comprise a first predetermined characteristic, while the shape, size, etc., may comprise a second predetermined characteristic.

In another example, first processing station 118 may be a printer, while the second processing station 120 may be a laser drilling station. In this event, the inspection unit 125 may be configured to sense printing indicia and/or percentage composition of laser drilled holes, to provide a signal to controller 110.1 for comparison against the respective standard.

In the case of a laser drilled hole, one or more of the inner layers of the article may be exposed. In this event, it may be possible to obtain spectral analysis of not only the outer surface of the article, to inspect for the composition of, e.g., gel coating and/or printed indicia, but also to inspect the various layers of the article that are subject to laser drilling, to analyze the composition of such layer or layers.

Figure 2:
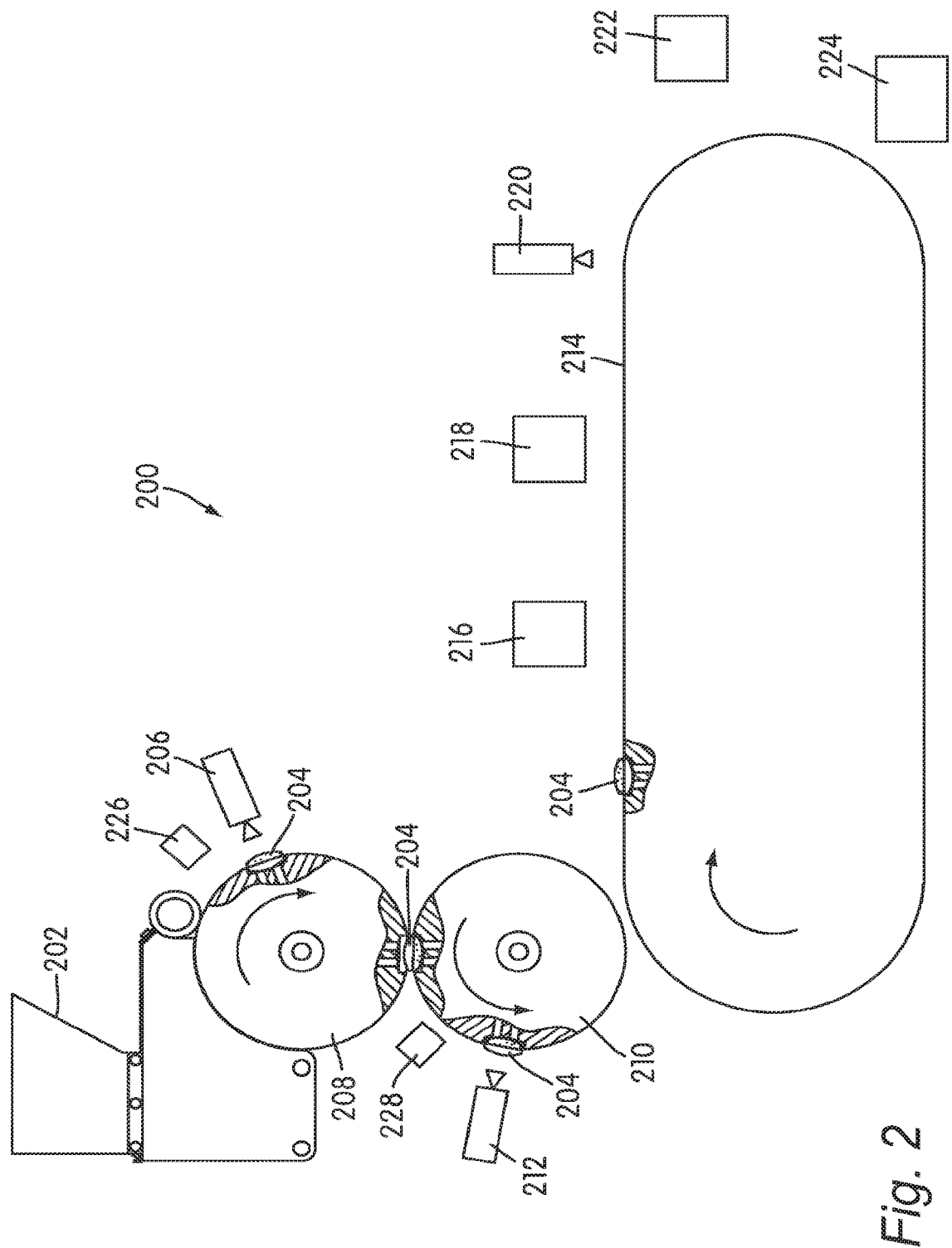
FIGS. 2 and 3 are alternative conveyer systems according to embodiments of the present invention.
Figure 3:
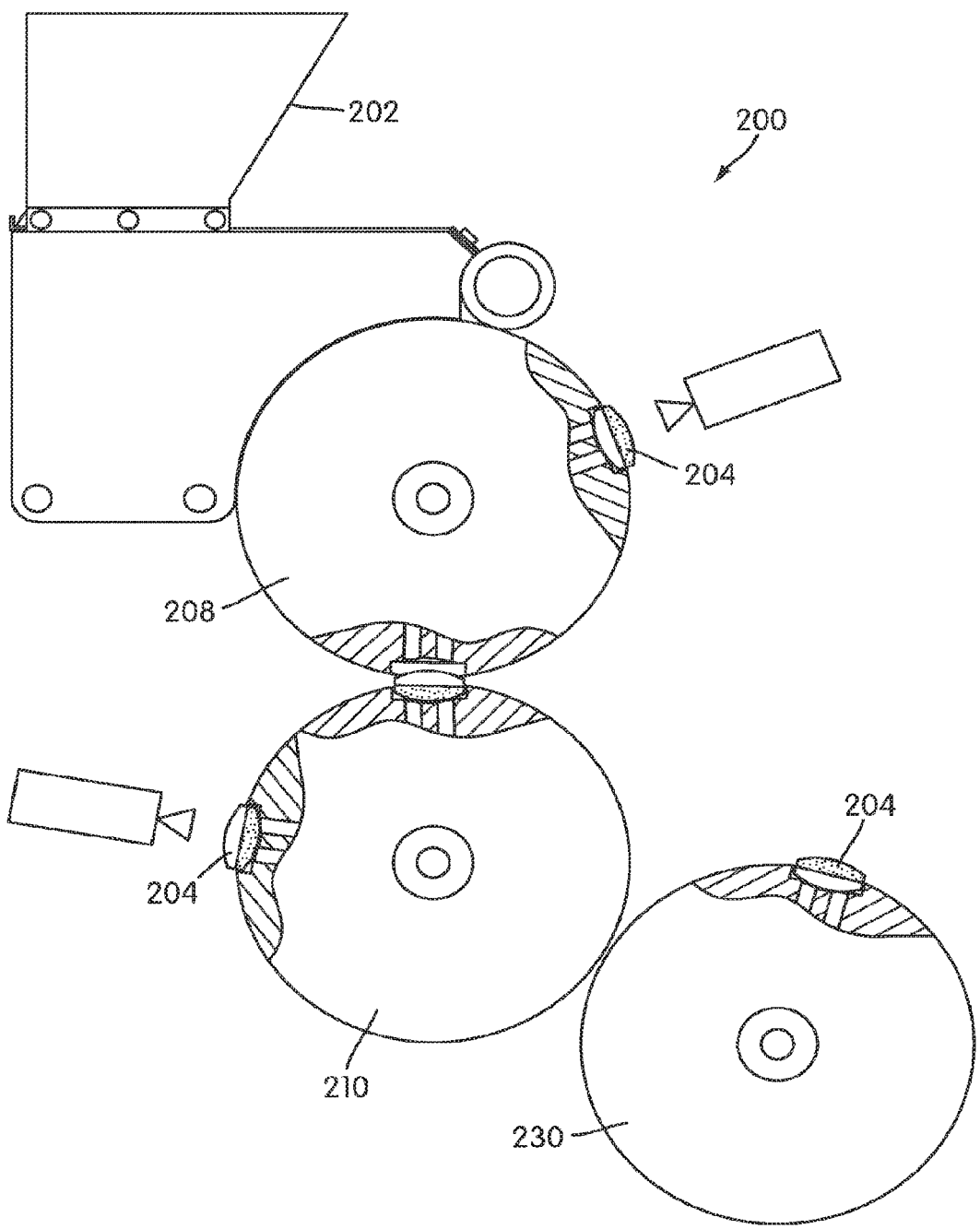

FIGS. 2 and 3 illustrate further embodiments of the present invention, in which a drum feed printer can also be used to sense both sides of an article, e.g., a tablet. For example, the article can be flipped over when being transferred from one drum to another drum.

As shown in FIG. 2, a drum feed system 200 includes a hopper 202 containing a plurality of articles to be processed, e.g., drilled, inspected, provided with indicia, etc., on one or both sides. Articles 204 from the hopper 202 have first and second sides with first and second predetermined characteristics that may be different from one another. For example, the sides may have a different color, and/or both sides may have a coating. A first inspection unit 206 is provided to sense the first side of the article as it is carried by a first feed drum 208 converging the article along a conveying path. A second feed drum 210 receives the article A from the first feed drum 208 to expose the second side of the article A to processing. A second inspection unit 212 inspects the second side of the article. The second feed drum 210 feeds the article to a conveyer mechanism 214, similar to that described above in relation to FIG. 1. The conveyer mechanism 214 may include one or more processing stations 216, 218, a third inspection unit 220, and suitable reject and accept bins 222, 224 like those shown in FIG. 1.

Further processing stations 226, 228 may be provided on the first and second feed drums 208, 210, respectively. For example, processing stations 226, 228 may provide coatings to the first and second sides of the article, while the processing station 216 provides indicia, e.g., printing, and the processing station 218 drills holes for time release purposes.

The first, second and third inspection units may be in the form of NIR spectroscopy sensors, as described above. The first inspection unit 206 may sense a composition of the first side of the article, the second inspection unit 212 may sense a composition of a second side of the article, and the third sensor 220 can sense the first side again, after the operation of processing stations 216 and 218. Each inspection unit may relate to the overall composition in comparison to the overall article, or each may relate to an isolated composition, e.g., printing indicia, gel coating, or laser drilling, etc. Moreover, the third unit 220 may sense the overall composition, while the first and second units 206, 212 may be configured for comparing only isolated characteristics/compositions. In addition, it should be noted that unit 206 can be eliminated as unit 220 inspects the same side of the article, although both are preferred for best results.

FIG. 3 shows a feed drum system which is similar to that shown in FIG. 2, and like reference numbers have been used to indicate like parts. However, the first feed drum 208 in FIG. 3 receives the articles 204 in a manner that seats the articles generally in the correct position. The articles are more accurately seated in the second feed drum 210, while a third feed drum 230 serves to re-expose the first side of the article for inspection/processing.

Bar Coding of Pellet-Shaped Articles

Figure 4:
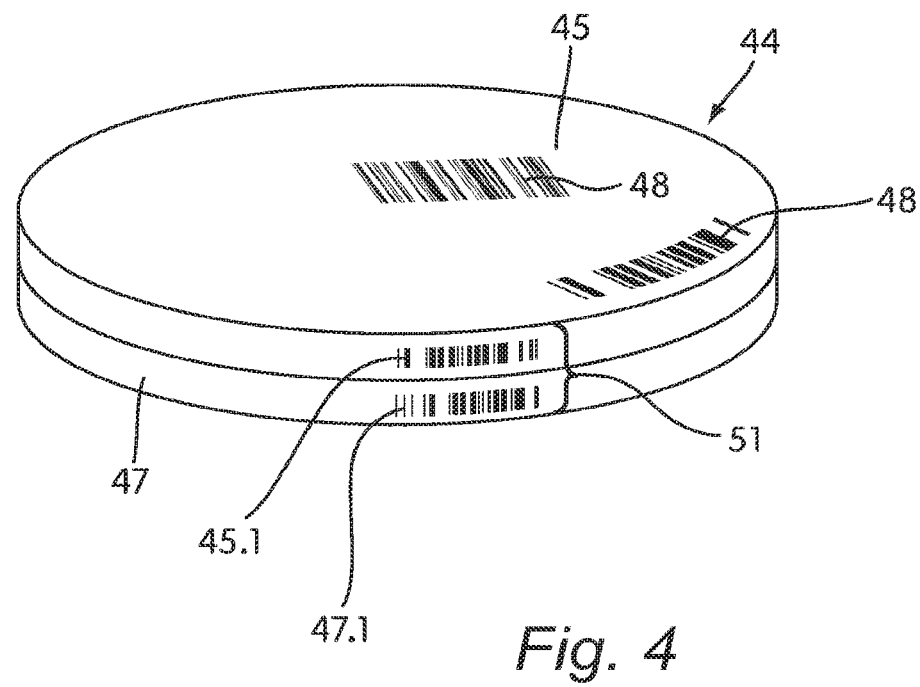
FIG. 4 is a perspective view illustrating a tablet-shaped article according to an embodiment of the present invention.
Figure 5:
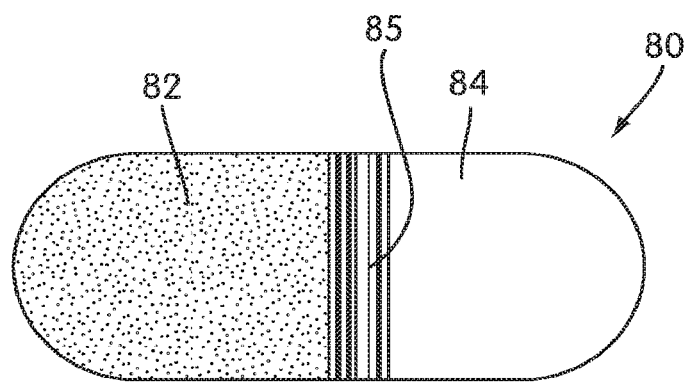
FIG. 5 is a perspective view illustrating a caplet or capsule-shaped article according to an embodiment of the present invention.

FIGS. 4 and 5 illustrate pellet-shaped articles that can be provided with a bar code. FIG. 4 schematically shows a tablet type article 44, which may be generally round, oval or lentil shaped and include a top surface 45 and a bottom surface 47, possibly made of dissimilar materials that are bonded to one another. Either or both of the surfaces 45, 47 may be provided with a bar code 48.

In one embodiment, the edge 51 of the article 44 could be provided with a pair of bar codes 45.1, 47.1. The bar codes 45.1 and 47.1 could be provided to the top and bottom surfaces 45, 47, respectively, before the surfaces are bonded to one another. If the codes 45.1, 47.1 do not match upon bonding, then the product would be rejected.

FIG. 5 shows a capsule or caplet 80 having first and second ends 82, 84. End 84 includes a circumferential bar code 85. Bar code 85 is formed such that the bars within the code extend about the circumference of the article. This is advantageous because the bar code can be read at any circumferential position of the article. Of course, the bar code can be formed such that the bars in the code wrap around the article in the manner shown in FIG. 4, i.e., parallel to the main longitudinal axis of the article.

In general, bar codes can include information to uniquely identify the product. For example, the bar code may include information regarding the manufacturer, batch, lot, time/date of manufacture, composition (e.g., the standard composition for the medicine, printing indicia, gel coating, laser drilled holes, etc.) etc. The bar code may include general information about the product as well. The bar code is machine readable by a scanner that may have access to a database that can be provided locally or remotely. Bar codes can take many forms, such as the examples provided in FIGS. 6 and 7. For example, the bar codes shown in FIGS. 4 and 5 may be any one or combination of a linear bar code, a stacked bar code, a 2D code, a uniform product code, a micro PDF code, a Smart code, an RSS limited code, an RSS limited composite code, an RSS stacked code, an RSS expanded code, and an RSS expanded composite code.

Figure 9:
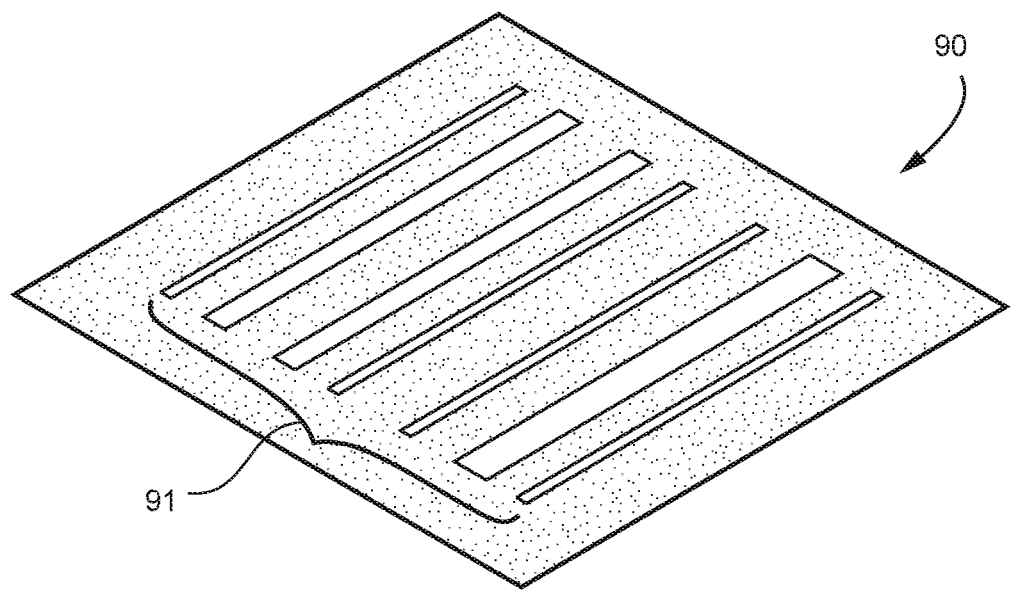
FIG. 9 illustrates a stencil with cut outs in the shape of a bar code.

The bar code may be applied to the article by contact or non-contact printing. In one example, the articles can be laser etched into the surface of the article. In one application, the bar code is invisible to the naked eye. For example, the articles may be provided with a clear coating, and the bar code provided by etching or removing a portion of the clear coating in the shape of a bar code. In another example, the laser may use a stencil 90 having cut outs 91 in the shape of a bar code, as shown in FIG. 9. In still another example, each article includes a photo resist layer in the shape of the negative image of the bar code. In yet another example, the bar code may be provided by use of an environmentally sensitive composition or coating that reacts when stimulated with certain light, temperature, etc.

Figures 7, 7A:
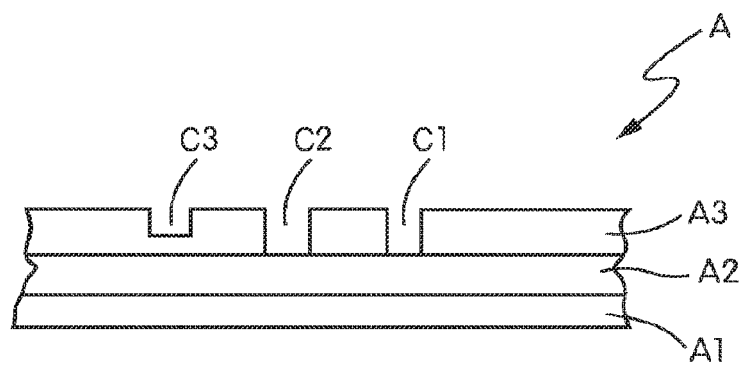
FIG. 7A illustrates a further embodiment according to the present invention.

FIG. 7A illustrates a partial cross sectional view of a portion of a pellet-shaped article A, e.g., a tablet, capsule, or caplet, that uses one or more of the above techniques to form the bar code. Article A includes a base substrate A1 that includes, e.g., medicine. One or more layers A2, A3 are provided over substrate A1. For example, layer A2 may be in the form of a secondary medicine, while layer A3 may be in the form of a coating, e.g., a sugar coating and/or gel coating. Of course, layers A2 and A3 are optional and not necessary. In another example, layer A3 may be in the form of a clear coating, as described above.

Figure 6:
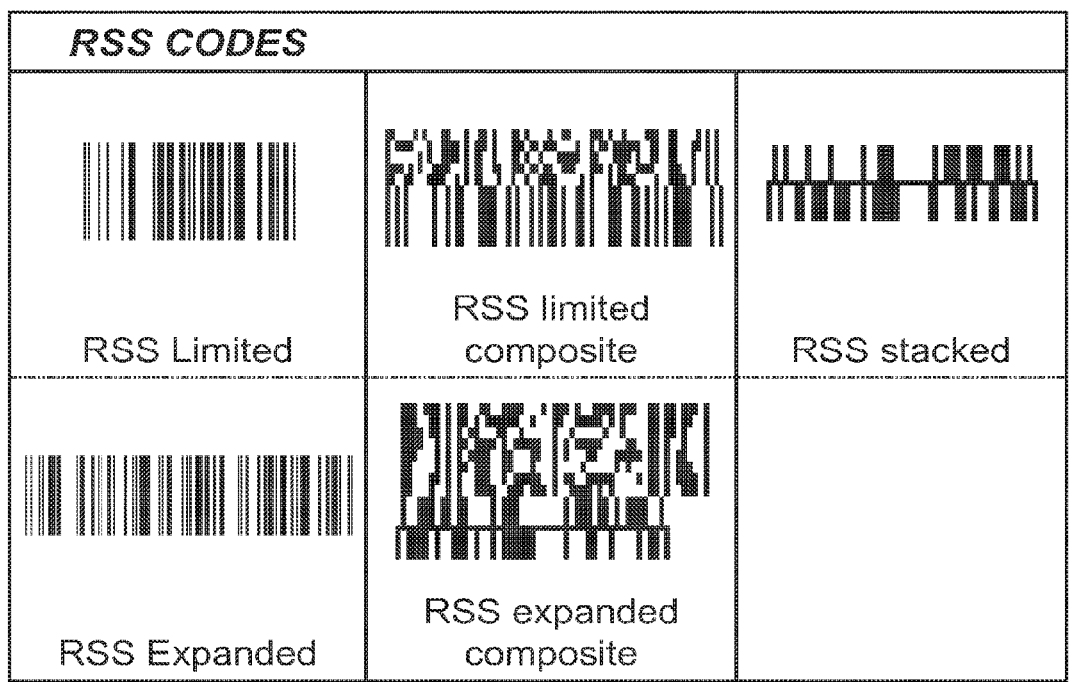
FIGS. 6 and 7 illustrate examples of bar codes according to aspects of the present invention.

The outmost layer, in this case A3, is provided with a plurality of cutouts C1, C2, C3 that correspond to the shape of a bar code, e.g., the bar codes shown in FIGS. 6-7. Cutouts can be created using a laser. As shown, cutouts C1 and C2 extend to but do not extend past the layer A2, although cutouts extending into layer A2, or even layer A1, are also contemplated. In this event, the cutouts could form not only a bar code, but could also function as a time release mechanism to slowly release medicine from layers A1 and/or A2. Layers A1 and/or A2 can be made with a dark color composition, in comparison with layer A3, to increase contrast and facilitate reading of the bar code. Of course, it may be desirable to conceal the bar code, in which case the layers A1, A2 and/or A3 can be made of the same color. In an alternative, cutouts can extend only partially through the layer, e.g., see cutout C3.

Figure 8:
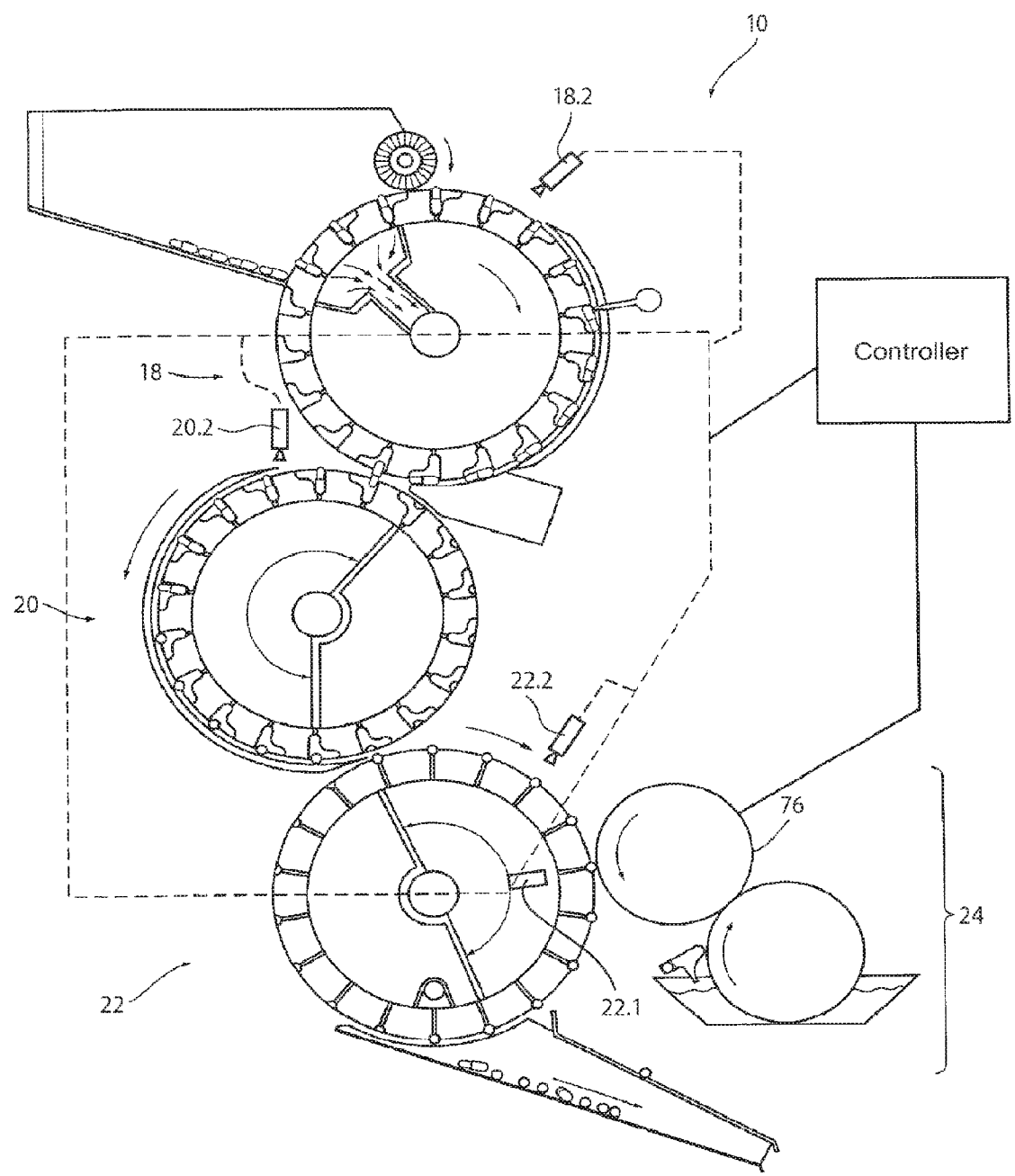
FIG. 8 illustrates a spin printer according to an embodiment of the present invention.

FIG. 8 illustrates a bar code printing unit 10 according to an embodiment of the present invention. The bar code printing unit 10 according to this embodiment is a spin printing unit which operates substantially as described in relation to U.S. Pat. No. 6,481,347, incorporated herein by reference in its entirety. Spin printer 10 includes a series of drums 18, 20, 22 which operate in a known manner to orient and print capsules or caplets. In the printing position, e.g., at drum 22, a printing unit 24 is provided to apply a machine-readable bar code to the articles, which results in an article (caplet/capsule) like that shown in FIG. 5. Transfer drum 76 imparts a spin on articles A, such that the bar code can be provide along the circumference of articles.

Figure 10:
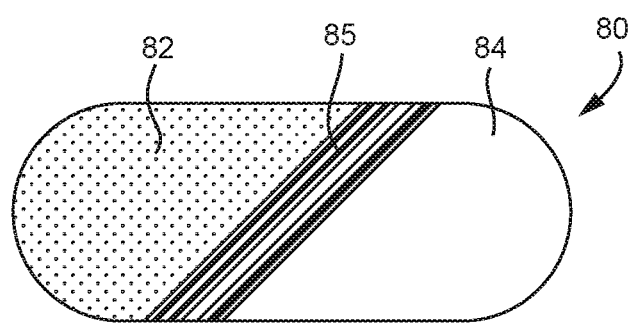
FIG. 10 is a perspective view illustrating a caplet or capsule-shaped article according to another embodiment of the present invention.

Of course, printer unit 24 could provide conventional printing indicia as well. In another alternative, a laser unit 22.1 could be provided on the inside of drum 22 to provide the bar code indicia as the articles spin, in which case printing unit 24 may or may not be present/operable. In one embodiment, the bar code is provided along the entire circumference of the article, although only a fraction of the circumference could be used. Also, the bar code could be provided in a spiral along the product axis, as shown in FIG. 10.

As shown in FIG. 8, one or more of the drums 18, 20, 22 can be provided with an NIR sensor 18.2, 20.2, and/or 22.2 for the purposes described above.

It can thus be appreciated that the objectives of the present invention have been fully and effectively accomplished. The foregoing specific embodiments have been provided to illustrate the structural and functional principles of the present invention and are not intended to be limiting. To the contrary, the present invention is intended to encompass all modifications, alterations, and substitutions within the spirit and scope of the present invention.

The invention claimed is:

1. A spin printer for providing bar codes on a surface of a plurality of capsules or a plurality of caplets, the spin printer comprising:
   at least a first drum unit that spins about a drum axis with each of said capsules or each of said caplets carried by the first drum unit and having a product axis oriented substantially parallel to the drum axis, the first drum unit being structured to allow spinning of each of said capsules or each of said caplets along the product axis; and
   a bar code unit to provide a machine-readable bar code on a circumferential surface of each of the capsules or each of the caplets as each of said capsules or each of said caplets is spun about the product axis,
   wherein the bar code unit includes a laser unit configured to etch the bar code into each of said capsules or each of said caplets while each of said capsules or each of said caplets is spinning.

2. A spin printer according to claim 1, wherein the laser unit includes a stencil having cut outs in the shape of the bar code.

3. A spin printer according to claim 1, wherein the bar code is provided along the entire circumference of the capsules or caplets.

4. A spin printer according to claim 1, wherein the bar code is provided in a spiral along the product axis.

5. An apparatus for applying a bar code to pellet-shaped articles, the pellet-shaped articles having an elongate shape, a first end, a second end, a longitudinal axis between the first end and the second end, and a circumference around the longitudinal axis, the apparatus comprising:
   a processing drum having a plurality of pockets to receive individual pellet-shaped articles; and
   a processing unit comprising a roller positioned adjacent to the processing drum such that the circumference of the roller is approximately tangential to the circumference of the processing drum, the roller being configured to engage and rotate each of the pellet-shaped articles within the corresponding pocket about the longitudinal axis of the pellet-shaped article,
   wherein the processing unit is configured to apply the bar code to the circumference of the pellet-shaped article while the pellet-shaped article is rotated by the roller within the corresponding pocket,
   wherein the processing unit further comprises a laser unit configured to etch the bar code into each pellet-shaped article while each pellet-shaped article is rotated by the roller within the corresponding pocket.

6. The apparatus of claim 5, wherein the bar code is applied about the entire circumference of each pellet-shaped article or a portion of the circumference of each pellet-shaped article.

7. The apparatus of claim 5, wherein the processing drum is configured to rotate about a processing drum axis,
   wherein each pellet-shaped article includes a product axis oriented substantially parallel to the processing drum axis, and
   wherein the laser unit is configured to etch the bar code on each pellet-shaped article in a spiral along the product axis.

8. A method for applying a bar code to pellet-shaped articles with an apparatus, the pellet-shaped articles having an elongate shape, a first end, a second end, a longitudinal axis between the first end and the second end, and a circumference around the longitudinal axis, the method comprising:
   receiving individual pellet-shaped articles within a corresponding one of a plurality of pockets of a processing drum that is rotating about an axis of rotation;
   engaging and rotating each of the pellet-shaped articles within the corresponding pocket about the longitudinal axis of the pellet-shaped article with a roller of a processing unit, the roller positioned adjacent to the processing drum such that the circumference of the roller is approximately tangential to the circumference of the processing drum; and
   applying the bar code with the processing unit to the circumference of the pellet-shaped article while the pellet-shaped article is rotated by the roller within the corresponding pocket,
   wherein the processing unit comprises a laser unit, and
   wherein applying the bar code comprises etching the bar code into each pellet-shaped article with the laser unit while each pellet-shaped article is rotated within the corresponding pocket.

9. The method of claim 8, further comprising etching the bar code about the entire circumference of each pellet-shaped article or a portion of the circumference of each pellet-shaped article.

10. The method of claim 8, wherein the processing drum is configured to rotate about a processing drum axis,
   wherein each pellet-shaped article includes a product axis oriented substantially parallel to the processing drum axis, and
   wherein the method further comprises etching the bar code on each pellet-shaped article in a spiral along the product axis.

* * * * *